(12) United States Patent
Chou

(10) Patent No.: US 8,407,820 B1
(45) Date of Patent: Apr. 2, 2013

(54) BUCKLE FOR SWIMMING/DIVING GOGGLES

(76) Inventor: Terry Chou, Tainan (TW)

( * ) Notice: Subject to any disclaimer, the term of this patent is extended or adjusted under 35 U.S.C. 154(b) by 83 days.

(21) Appl. No.: 13/242,161

(22) Filed: Sep. 23, 2011

(51) Int. Cl.
*A63B 33/00* (2006.01)
*A61F 9/02* (2006.01)

(52) U.S. Cl. .................................. 2/448; 2/426; 2/428

(58) Field of Classification Search .................. None
See application file for complete search history.

(56) References Cited

U.S. PATENT DOCUMENTS

| | | | | |
|---|---|---|---|---|
| 4,607,398 A * | 8/1986 | Faulconer | | 2/452 |
| 5,459,882 A * | 10/1995 | Yamamoto | | 2/428 |
| 5,555,571 A * | 9/1996 | McCaffrey | | 2/428 |
| 5,566,427 A * | 10/1996 | Lathrop | | 24/169 |
| 5,617,588 A * | 4/1997 | Canavan et al. | | 2/428 |
| 5,657,493 A * | 8/1997 | Ferrero et al. | | 2/428 |
| 5,727,259 A * | 3/1998 | Kawamata | | 2/452 |
| 5,915,540 A * | 6/1999 | Chou | | 2/428 |
| 5,956,778 A * | 9/1999 | Godoy | | 2/428 |
| 6,292,983 B1 * | 9/2001 | Giaquinta et al. | | 24/68 R |
| 6,446,272 B1 * | 9/2002 | Lee | | 2/428 |
| 6,499,148 B2 * | 12/2002 | Chou | | 2/428 |
| 6,516,474 B2 * | 2/2003 | Chou | | 2/428 |
| 6,691,377 B2 * | 2/2004 | Pan | | 24/170 |
| 6,691,378 B1 * | 2/2004 | Chou | | 24/170 |
| 6,694,532 B2 * | 2/2004 | Chen | | 2/428 |
| 6,832,394 B1 * | 12/2004 | Chiang | | 2/428 |
| 7,007,311 B2 * | 3/2006 | Chiang | | 2/448 |
| 7,020,905 B2 * | 4/2006 | Chiang | | 2/448 |
| 7,055,182 B2 * | 6/2006 | Chiang | | 2/450 |
| 7,146,653 B2 * | 12/2006 | Chou | | 2/426 |
| 7,275,536 B2 * | 10/2007 | Godoy | | 128/207.11 |
| 7,296,306 B2 * | 11/2007 | Chou | | 2/448 |
| 7,571,520 B2 * | 8/2009 | Shiue | | 24/265 BC |
| 7,640,633 B2 * | 1/2010 | Chou | | 24/68 E |
| 7,665,190 B2 * | 2/2010 | Weng | | 24/170 |
| 7,823,226 B2 * | 11/2010 | Chou | | 2/448 |
| 7,836,561 B2 * | 11/2010 | Vaccaro et al. | | 24/68 E |
| 7,856,674 B2 * | 12/2010 | Chou | | 2/452 |
| 7,921,523 B2 * | 4/2011 | Chou | | 24/170 |
| 7,966,701 B2 * | 6/2011 | Shiue | | 24/170 |
| 8,201,278 B2 * | 6/2012 | Chou | | 2/426 |
| 8,312,603 B2 * | 11/2012 | Chou | | 24/170 |
| 2002/0152543 A1 * | 10/2002 | Chou | | 2/428 |
| 2003/0233702 A1 * | 12/2003 | Chen | | 2/428 |
| 2003/0233737 A1 * | 12/2003 | Chen-Lieh | | 24/170 |
| 2006/0010585 A1 * | 1/2006 | Chiang | | 2/426 |
| 2006/0015990 A1 * | 1/2006 | Chiang | | 2/426 |
| 2007/0157373 A1 * | 7/2007 | Chou | | 2/448 |
| 2008/0204653 A1 * | 8/2008 | Fielding | | 351/156 |
| 2008/0244875 A1 * | 10/2008 | Chou | | 24/170 |
| 2009/0100645 A1 * | 4/2009 | Weng | | 24/170 |

(Continued)

*Primary Examiner* — Bobby Muromoto, Jr.

(57) ABSTRACT

A buckle includes a base having a plate. A compartment is defined between upper and lower walls of the plate. A front end of a pressing board is engaged with a front end of the plate. A rear end of the pressing board includes a pressing face and two guiding faces. An operating button is received in the compartment and includes a resilient section having upper and lower buttons extending through slots in the upper and lower walls. The operating button can be pressed to cause two pressing surfaces of the resilient section to press against the guiding faces of the pressing board for moving the pressing board rearward relative to the base, disengaging the pressing face of the pressing board from the head strap to permit the head strap to move in a reverse direction for loosening the head strap.

5 Claims, 10 Drawing Sheets

U.S. PATENT DOCUMENTS

| | | | | |
|---|---|---|---|---|
| 2009/0113608 A1* | 5/2009 | Chou | | 2/452 |
| 2009/0122258 A1* | 5/2009 | Fielding, Jr. | | 351/156 |
| 2009/0205115 A1* | 8/2009 | Chou | | 2/452 |
| 2011/0258761 A1* | 10/2011 | Chou | | 2/445 |
| 2011/0302702 A1* | 12/2011 | Chiang | | 2/442 |
| 2012/0222202 A1* | 9/2012 | Chiang | | 2/452 |
| 2012/0233825 A1* | 9/2012 | Chou | | 24/68 E |
| 2012/0266418 A1* | 10/2012 | Chou | | 24/191 |

* cited by examiner

A-A

B-B

C-C

BUCKLE FOR SWIMMING/DIVING GOGGLES

BACKGROUND OF THE INVENTION

The present invention relates to a buckle for swimming/diving goggles and, more particularly, to a buckle for swimming/diving goggles allowing easy adjustment of a length of a head strap while providing stable operation.

Swimming goggles generally include two lenses, two frames, a bridge, a buckle, and a head strap. The buckle allows adjustment of a length of the head strap. FIG. 10 shows a conventional buckle 1' including an end with an engagement portion 11' for engagement with a body 3' of a pair of swimming goggles. The other end of the buckle 1' includes a coupling portion 12' for coupling with a soft head strap 2'. The coupling portion 12' includes pegs 121' and 122' at an intermediate portion thereof. A notch 123' is defined in a front end of the coupling portion 12'. The head strap 2' is extended between the notch 123' and the peg 121' and wound around the pegs 121' and 122' and extended between the notch 123' and the peg 121' again, fixing the head strap 2'. When adjustment of the head strap 2' is required, the user removes the body 3' from his or her head, loosens the head strap 2', and adjusts the length of the head strap 2', which is troublesome and time-consuming. However, the length of the head strap 2' after adjustment may not fit the head of the user. As a result, readjustment of the head strap 2' is required when the head strap 2' is either too tight or too loose. Furthermore, the head strap 2' deforms significantly at the bends wound around the pegs 121' and 122'.

U.S. Pat. No. 6,832,394 discloses swimming goggles including a resilient button that can be pressed to control adjustment of a length of the head strap. However, the resilient button is pressed in a direction against the head, causing discomfort to the user.

U.S. Pat. No. 7,020,905 discloses a swimming goggle including head fasteners respectively connected with left and right frames and adjusting apparatuses for adjusting the head fasteners. Each adjusting apparatus includes a base, a cover, a biasing arm, two operating buttons, and a flexible arcuate plate. A shaft is received in a shaft hole of the base. In assembly, the head fastener is pulled from an inlet of the base, around the shaft, and out of an outlet of the base. The biasing arm, the operating buttons, and the arcuate plate are assembled together. The biasing arm has a biasing end for cooperating with the shaft to engage with a stop slot of a corresponding head fastener. The arcuate plate has an end connecting with sides of the operating buttons. The opposite end of the arcuate plate connects with an end of the biasing arm opposite to the biasing end for providing return force. The operating buttons are assembled in grooves of the cover and have ends projecting slightly beyond the sides of the cover for convenient performance. The basing end of the biasing arm engages with the stop slot of a corresponding head fastener such that the head fastener can not move toward the inlet, but can only move out of the outlet. The operating buttons can be pressed to cause an unlocking block of each operating button to move the biasing end of the biasing arm so as to disengage the biasing arm from the stop slot. The head fasteners are, thus, free to allow adjustment. The operating buttons are pressed in a direction without causing discomfort to the head of the user. However, the biasing arm, the arcuate plate, and the buttons are integrally formed such that deformation of the arcuate plate would not be easy if the arcuate plate is made of a rigid material. On the hand, the arcuate plate can deform easily when the operating buttons are pressed if the arcuate plate is made of a soft material. However, the soft arcuate plate can not reliably retain the basing end of the biasing arm in the stop slot of the head fastener. Furthermore, the arcuate plate provides the returning force for only side of the corresponding operating button, and the other side of the operating button is not supported. The returning forces after releasing the operating buttons are not even, failing to provide stable operation.

BRIEF SUMMARY OF THE INVENTION

An objective of the present invention is to provide a buckle for swimming goggles with operational convenience while providing stable operation.

A buckle for swimming/diving goggles according to the present invention is adapted to be mounted to a side of a body of the swimming/diving goggles and adapted to mount a head strap. The head strap includes a plurality of teeth on a side thereof. Each of the plurality of teeth of the head strap includes an inclined guiding face and an engagement face. The buckle includes a base having a plate with front and rear ends. The rear end of the plate includes an insertion hole and a partitioning plate. The head strap is adapted to be extended through the insertion hole and wound around the partitioning plate. The plate includes upper and lower walls each having a slot. A compartment is defined between the upper and lower walls. A pressing board includes a front end and a rear end. The front end of the pressing board is engaged with the front end of the plate of the base. The rear end of the pressing board includes a pressing section corresponding to the partitioning plate. The pressing section includes a pressing face on a rear side thereof. The pressing section further includes first and second guiding faces on a front side thereof. An operating button is received in the compartment of the base and includes a resilient section. An upper button is formed on a top side of the resilient section and extended through the slot of the upper wall. A lower button is formed on a bottom side of the resilient section and extended through the slot of the lower wall. The resilient section includes first and second pressing surfaces corresponding to the first and second guiding faces of the pressing section of the pressing board.

When the operating button is not pressed, the head strap is movable in a first direction to tighten the head strap and not movable in a second direction reverse to the first direction. The engagement face of one of the plurality of the teeth of the head strap is engaged with the pressing face of the pressing section of the pressing board to retain the head strap. On the other hand, when the operating button is pressed, the first and second pressing surfaces of the resilient section of the operating button press against the first and second guiding faces of the pressing board to move the pressing board rearward relative to the base, disengaging the pressing face of the pressing board from the engagement face of the head strap to permit the head strap to move in the second direction for loosening the head strap.

The pressing board is mounted to an outer side of the body. The operating button has rigidity lower than the pressing board.

The first and second guiding faces are inclined and formed on top and bottom faces of the front side of the pressing section. The resilient section includes upper and lower beams each having a length larger than the slots of the upper and lower walls. The upper button is formed on a top side of the upper beam, and the lower button is formed on a bottom side of the lower beam. Each of the upper and lower beams includes first and second ends. The first pressing surface is formed on the first end of the upper beam, and the second pressing surface is formed on the first end of the lower beam. A first arcuate plate extends between the first ends of the upper and lower beams, and a second arcuate plate extends between the second ends of the upper and lower beams. The first and second arcuate plates are spaced from each other by a spacing to allow deformation of the first and second arcuate plates.

The first and second arcuate plates have curvatures representing a hyperbola, and the spacing between the first and second arcuate plates is reduced when the operating button is operated.

The front end of the plate of the base includes a plurality of pegs. The front end of the pressing board includes a plurality of coupling holes. The plurality of pegs of the base is extended through through-holes in the side of the body into the plurality of coupling holes of the pressing board.

The present invention will become clearer in light of the following detailed description of illustrative embodiments of this invention described in connection with the drawings.

DETAILED DESCRIPTION OF THE INVENTION

Figure 1:
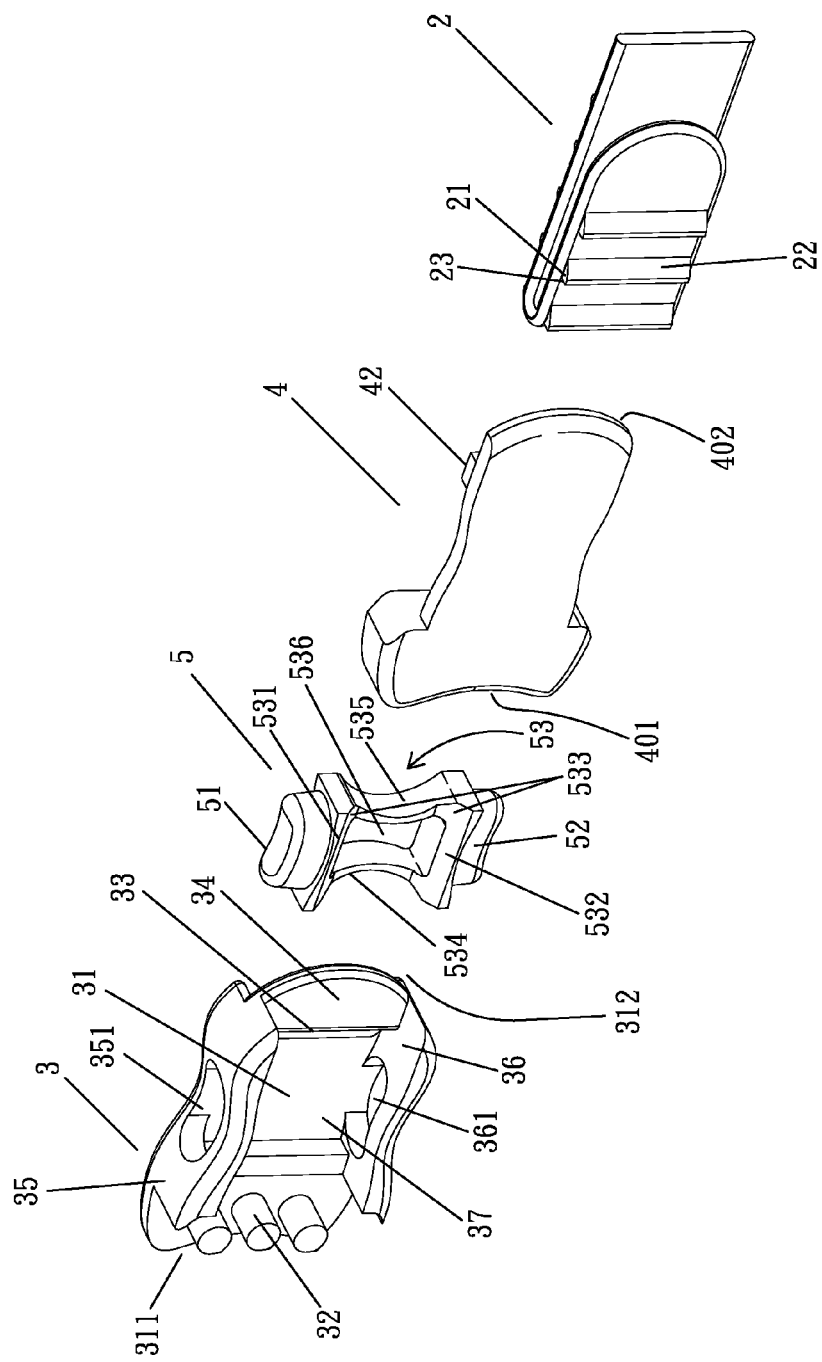
FIG. 1 shows an exploded, perspective view of a buckle for swimming/diving goggles according to the present invention.
Figure 2:
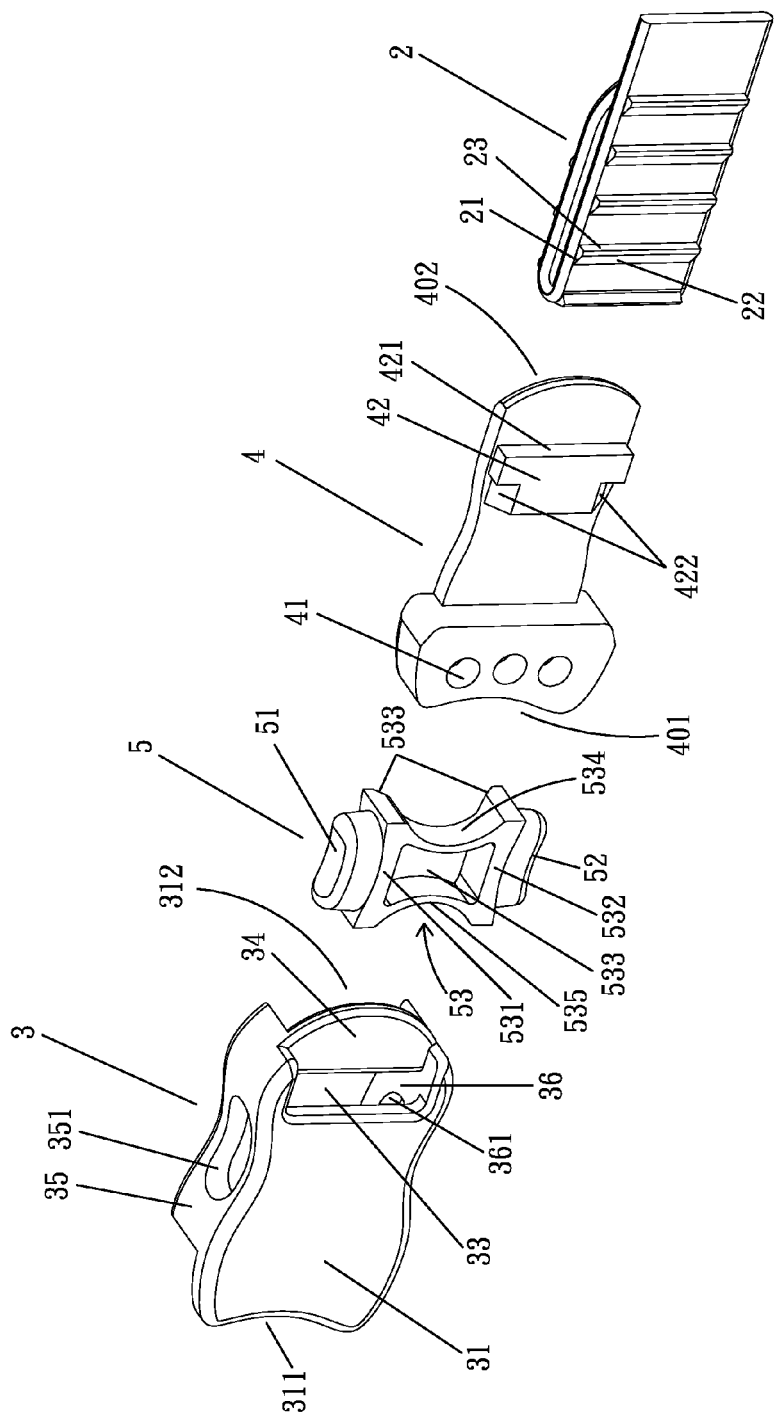
FIG. 2 shows another exploded, perspective view of the buckle of FIG. 1.
Figure 3:
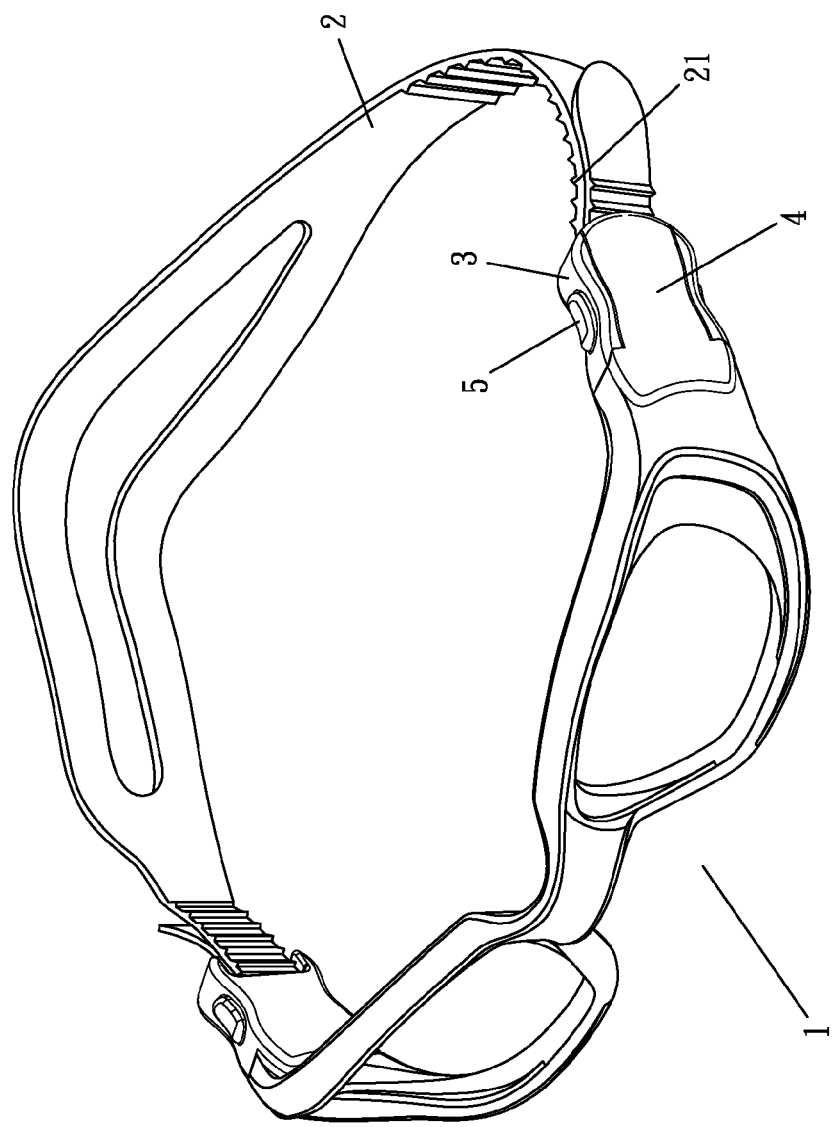
FIG. 3 shows a perspective view of swimming/diving goggles with the buckle of FIG. 1.

With reference to FIGS. 1-6, a buckle according to the present invention is mounted to a side of a body 1 of swimming/diving goggles for coupling with a head strap 2 that includes a plurality of teeth 21 on a side thereof. Each tooth 21 of the head strap 2 includes an inclined guiding face 22 and an engagement face 23. In the form shown, another buckle is mounted to the other side of the body 1.

The buckle according to the present invention includes a base 3, a pressing board 4, and an operating button 5. The base 3 includes a plate 31 having a front end 311 and a rear end 312. The front end 311 includes a plurality of pegs 32. The rear end 312 includes an insertion hole 33 and a partitioning plate 34. The head strap 2 is extended through the insertion hole 33 and wound around the partitioning plate 34. The plate 31 includes upper and lower walls 35 and 36, with a compartment 37 defined between the upper and lower walls 35 and 36. Each of the upper and lower walls 35 and 36 has a slot 351, 361 in communication with the compartment 37.

The pressing board 4 includes a front end 401 and a rear end 402. The front end 401 includes a plurality of coupling holes 41. The pegs 32 of the base 3 are extended through through-holes 11 of the body 1 into the coupling holes 41. The rear end 402 includes a pressing section 42 corresponding to the partitioning plate 34. The pressing section 42 includes a pressing face 421 on a rear side thereof. The pressing section 42 further includes an inclined guiding face 422 on each of top and bottom faces of a front side thereof.

The rigidity of the operating button 5 is smaller than that of the pressing board 4. The operating button 5 is mounted in the compartment 37 of the base 3. An upper button 51 is provided on a top side of the operating button 5 and extended through the slot 351 in the upper wall 35. A lower button 52 is provided on a bottom side of the operating button 5 and extended through the slot 361 in the lower wall 36. A resilient section 53 is located between the upper and lower buttons 51 and 52 and includes upper and lower beams 531 and 532 each having a length larger than that of the slots 351 and 361. The upper button 51 is formed on the top side of the upper beam 531, and the lower button 52 is formed on the bottom side of the lower beam 532. Each of the upper and lower beams 531 and 532 includes first and second ends, with a pressing surface 533 on the first end thereof. The pressing surfaces 533 correspond to the guiding faces 422 of the pressing board 4. A first arcuate plate 534 extends between the first ends of the upper and lower beams 531 and 532. A second arcuate plate 535 extends between the second ends of the upper and lower beams 531 and 532. The first and second arcuate plates 534 and 535 are spaced from each other by a spacing 536 to allow deformation of first and second arcuate plates 534 and 535. Note that the curvatures of the first and second actuate plates 534 and 535 representing a hyperbola. When the operating button 5 is pressed by the upper and lower buttons 51 and 52, the spacing 536 between the first and second arcuate plates 534 and 535 is reduced. This can reduce the volume of the base 3.

Figure 4:
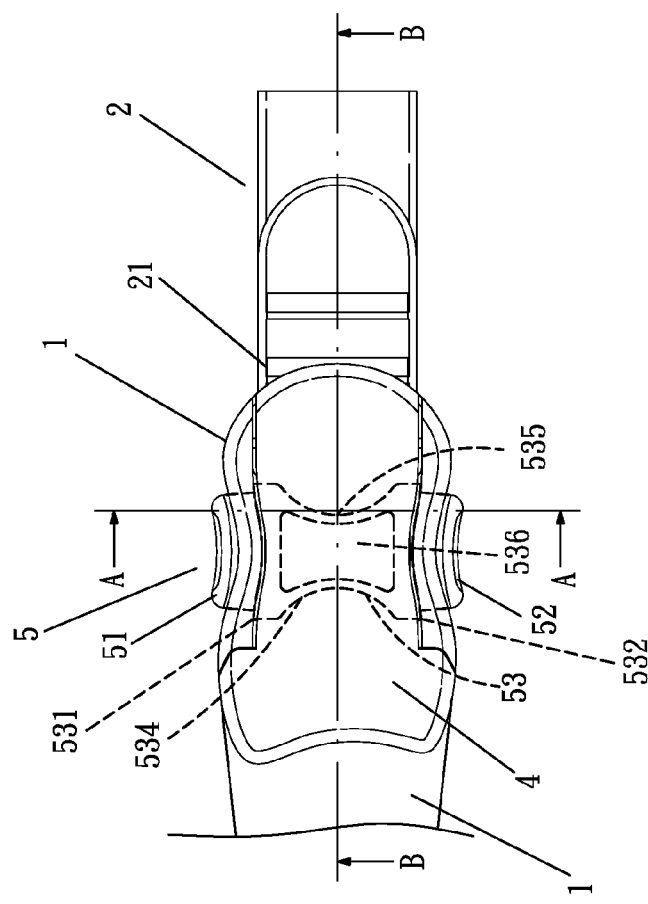
FIG. 4 shows a partial, side view of the swimming/diving goggles of FIG. 3.
Figure 5:
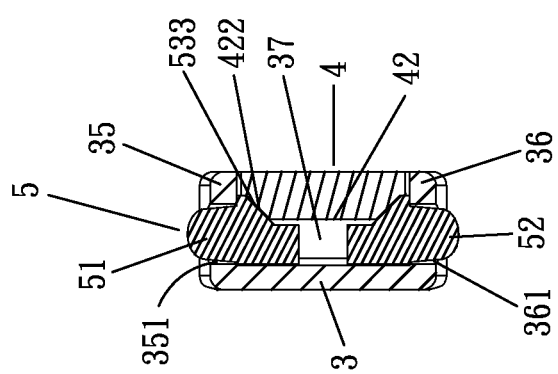
FIG. 5 shows a cross sectional view taken along section line A-A of FIG. 4.
Figure 6:
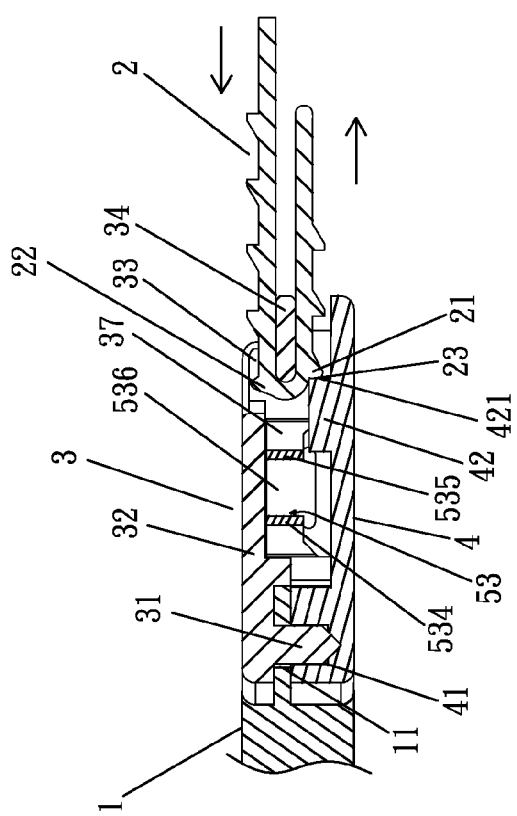
FIG. 6 shows a cross sectional view taken along section line B-B of FIG. 4.

With reference to FIGS. 4-6, due to provision of the inclined guiding face 22 on each tooth 21 of the head strap 2, the head strap 2 can only be pulled in a direction shown by the arrows in FIG. 6 to tighten the head strap 2 when the operating button 5 is not pressed. The pressing face 421 of the pressing section 42 of the pressing board 4 presses against the engagement face 23 of one of the teeth 21 to fix the tightness of the head strap 2. Since the pressing board 4 is harder than the operating button 5, reliable positioning can be provided by the engagement between the pressing face 421 of the pressing section 42 and the engagement face 23 of the tooth 21 of the head strap 2.

Figure 7:
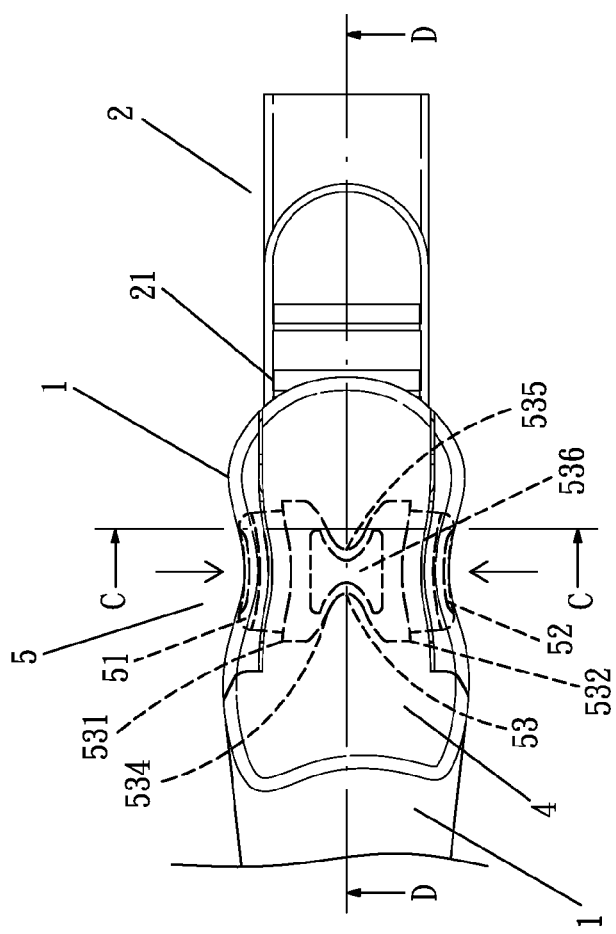
FIG. 7 shows a view similar to FIG. 4, with an operating button pressed.
Figure 8:
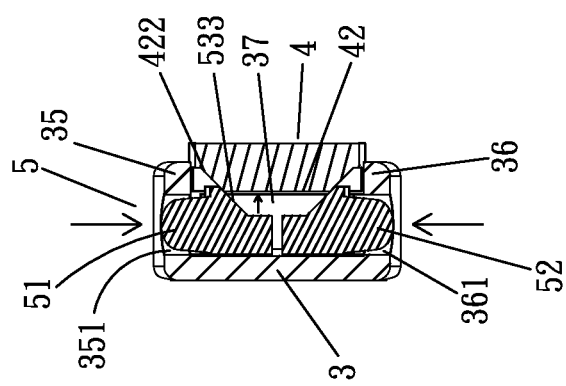
FIG. 8 shows a cross sectional view taken along section line C-C of FIG. 7.
Figure 9:
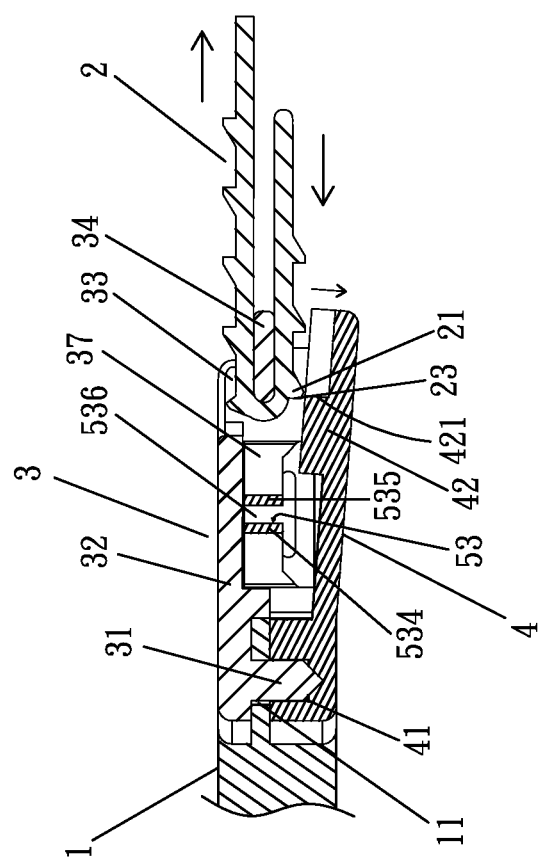
FIG. 9 shows a cross sectional view taken along section line D-D of FIG. 3.
Figure 10:
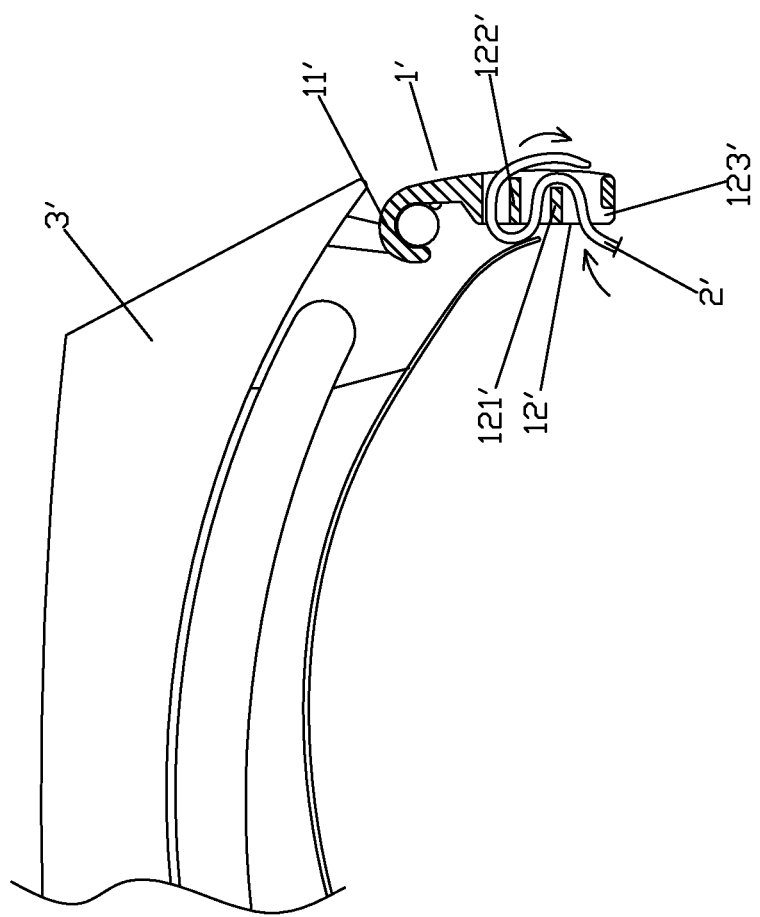
FIG. 10 shows a portion of a pair of conventional swimming goggles.

With reference to FIGS. 7-9, when the user intends to loosen the head strap 2, the user presses the operating button 5 by pressing the upper and lower buttons 51 and 523 toward each other, causing the pressing surfaces 533 to press against the guiding faces 422 of the pressing board 4. The pressing board 4 moves rearward relative to the base 3, disengaging the pressing face 421 from the engagement face 23 of the head strap 2. Thus, the head strap 2 can be moved in a reverse direction for loosening purposes.

By provision of the upper and lower buttons 51 and 52 that are pressed in a direction without imparting force to the head of the user, operating comfort is provided. Furthermore, the rigidity of the operating button 5 is smaller than the pressing board 4 to provide comfort and convenience during pressing of the upper and lower buttons 51 and 52. Further, the first and second arcuate plates 534 and 535 between the upper and lower beams 531 and 532 allow even compression and resilient restitution of the resilient section 53, providing enhanced stable operation.

In a case that the rigidity of the operating button 5 is not smaller than that of the pressing board 4, the reliable positioning effect for the head strap 2 can also be provided. Furthermore, the pressing surfaces 533 do not have to be arcuate as shown, and the pressing board 4 can still be moved rearward by operating the operating button 5. Likewise, the guiding faces 422 do not have to be arcuate as shown, while the pressing surfaces 533 are arcuate. In this case, the pressing board 4 can still be moved rearward by operating the operating button 5.

Although specific embodiments have been illustrated and described, numerous modifications and variations are still possible without departing from the essence of the invention. The scope of the invention is limited by the accompanying claims.

The invention claimed is:

1. A buckle for swimming/diving goggles, with the buckle adapted to be mounted to a side of a body of the swimming/diving goggles and adapted to mount a head strap, with the head strap including a plurality of teeth on a side thereof, with each of the plurality of teeth of the head strap including an inclined guiding face and an engagement face, with the buckle comprising:

a base including a plate having front and rear ends, with the rear end of the plate including an insertion hole and a partitioning plate, with the head strap adapted to be extended through the insertion hole and wound around the partitioning plate, with the plate including upper and lower walls each having a slot, with a compartment defined between the upper and lower walls;

a pressing board including a front end and a rear end, with the front end of the pressing board engaged with the front end of the plate of the base, with the rear end of the pressing board including a pressing section corresponding to the partitioning plate, with the pressing section including a pressing face on a rear side thereof, with the pressing section further including first and second guiding faces on a front side thereof; and an operating button received in the compartment of the base, with the operating button including a resilient section, with an upper button formed on a top side of the resilient section and extended through the slot of the upper wall, with a lower button formed on a bottom side of the resilient section and extended through the slot of the lower wall, with the resilient section including first and second pressing surfaces corresponding to the first and second guiding faces of the pressing section of the pressing board, wherein with the operating button not pressed, the head strap is movable in a first direction to tighten the head strap and not movable in a second direction reverse to the first direction, with the engagement face of one of the plurality of the teeth of the head strap engaged with the pressing face of the pressing section of the pressing board to retain the head strap, wherein with the operating button pressed, the first and second pressing surfaces of the resilient section of the operating button press against the first and second guiding faces of the pressing board to move the pressing board rearward relative to the base, disengaging the pressing face of the pressing board from the engagement face of the head strap to permit the head strap to move in the second direction for loosening the head strap.

2. The buckle for swimming/diving goggles as claimed in claim 1, with the pressing board mounted to an outer side of the body, with the operating button having rigidity lower than the pressing board.

3. The buckle for swimming/diving goggles as claimed in claim 1, with the first and second guiding faces being inclined and formed on top and bottom faces of the front side of the pressing section, with the resilient section including upper and lower beams each having a length larger than the slots of the upper and lower walls, with the upper button formed on a top side of the upper beam, with the lower button formed on a bottom side of the lower beam, with each of the upper and lower beams including first and second ends, with the first pressing surface formed on the first end of the upper beam, with the second pressing surface formed on the first end of the lower beam, with a first arcuate plate extending between the first ends of the upper and lower beams, with a second arcuate plate extending between the second ends of the upper and lower beams, with the first and second arcuate plates spaced from each other by a spacing to allow deformation of the first and second arcuate plates.

4. The buckle for swimming/diving goggles as claimed in claim 3, with the first and second arcuate plates having curvatures representing a hyperbola, with the spacing between the first and second arcuate plates being reduced when the operating button is operated.

5. The buckle for swimming/diving goggles as claimed in claim 3, with the front end of the plate of the base including a plurality of pegs, with the front end of the pressing board including a plurality of coupling holes, with the side of the body including through-holes, with the plurality of pegs of the base extended through the through-holes of the body into the plurality of coupling holes of the pressing board.

\* \* \* \* \*